United States Patent
Taylor et al.

(10) Patent No.: US 8,886,330 B2
(45) Date of Patent: Nov. 11, 2014

(54) METHOD AND APPARATUS FOR COCHLEAR IMPLANT SURGERY

(76) Inventors: Russell H. Taylor, Severna Park, MD (US); Wade Wei-De Chien, Potomac, MD (US); Iulian Iordachita, Towson, MD (US); John Niparko, Glen Arm, MD (US)

( * ) Notice: Subject to any disclaimer, the term of this patent is extended or adjusted under 35 U.S.C. 154(b) by 247 days.

(21) Appl. No.: 13/238,903

(22) Filed: Sep. 21, 2011

(65) Prior Publication Data
US 2012/0071890 A1 Mar. 22, 2012

Related U.S. Application Data

(60) Provisional application No. 61/384,940, filed on Sep. 21, 2010.

(51) Int. Cl.
*A61B 19/00* (2006.01)
*A61B 5/00* (2006.01)
*A61N 1/05* (2006.01)
*A61B 17/34* (2006.01)

(52) U.S. Cl.
CPC ............. *A61B 5/6844* (2013.01); *A61N 1/0541* (2013.01); *A61B 19/201* (2013.01); *A61B 2019/5251* (2013.01); *A61B 2019/507* (2013.01); *A61B 5/6817* (2013.01); *A61B 2017/3407* (2013.01)
USPC ................. 607/55; 607/56; 607/57; 607/115; 607/116; 607/118; 607/137

(58) Field of Classification Search
CPC ................... A61B 19/5244; A61B 2019/5268; A61B 2019/5483; A61B 5/06; A61B 2019/507; A61B 1/00158; A61B 2019/5238; A61B 2019/5295; A61B 5/1128; A61B 5/7285; A61B 6/541; A61B 2019/505; A61B 5/05; A61B 19/54; A61B 5/0084; A61B 5/0536; A61B 5/6814; A61B 5/6838; A61B 5/742; A61B 5/042; A61B 5/686; A61B 6/482; A61B 6/0583; A61B 6/14503; A61B 6/1459; A61B 6/1473; A61B 6/14865; A61B 6/6817; A61B 2019/2211; A61B 5/0215; A61B 5/04; A61B 5/6844; A61N 1/36032; A61N 1/05; A61N 1/0541; A61N 1/02; A61N 1/36017; A61N 1/3605; A61N 1/08; A61N 1/372; G06F 19/3418; A61M 2021/0027; A61M 21/00; A61M 2205/04; A61F 11/00; G01R 33/285; G01R 33/5608
USPC ............ 607/1–2, 55–57, 115–116, 118, 137; 606/129
See application file for complete search history.

(56) References Cited

U.S. PATENT DOCUMENTS 6,968,238 B1 * 11/2005 Kuzma .......................... 607/137
2004/0122446 A1   6/2004 Solar
(Continued)

FOREIGN PATENT DOCUMENTS

WO   WO-2006/048097 A1   5/2006

OTHER PUBLICATIONS

"Statistics about Hearing, Balance, Ear Infections, and Deafness," Jun. 10, 2010, [online], [retrieved on May 14, 2012] Website URL: ,http://www.nidcd.nih.gov/health/statistics/hearing.asp#1,2010>, 16pp.

(Continued)

*Primary Examiner* — Deborah Malamud
(74) *Attorney, Agent, or Firm* — Venable LLP; Henry J. Daley; F. Brock Riggs

(57) ABSTRACT

A system for cochlear implant surgery includes a reference device having at least a portion adapted to be arranged at a fixed position relative to a cochlea of a patient to provide a reference position, an image acquisition and processing system adapted to acquire an image of at least a portion of the cochlea relative to the reference position and to provide an implant plan based at least partially on the acquired image, and an implant system adapted for implanting a cochlear lead array using the reference position and the implant plan.

27 Claims, 8 Drawing Sheets

(56) References Cited

U.S. PATENT DOCUMENTS

| | | |
|---|---|---|
| 2006/0167472 A1 | 7/2006 | Hong et al. |
| 2006/0247513 A1 | 11/2006 | Wang et al. |
| 2006/0247517 A1 | 11/2006 | Labadie et al. |
| 2011/0052503 A1 | 3/2011 | Almen et al. |

OTHER PUBLICATIONS

Balicki et al., "Micro-force Sensing in Robot Assisted Membrane Peeling for Vitreoretinal Surgery", in Medical Image Computing and Computer-Assisted Intervention (MICCAI), Beijing, Sep. 2010, pp. 303-310.

Berkelman et al., "Performance Evaluation of a Cooperative Manipulation Microsurgical Assistant Robot Applied to Stapedotomy", in Medical Image Computing and Computer-Assisted Interventions (MICCAI 2001), Utrecht, 2001, pp. 1426-1429.

Briggs et al., "Development and evaluation of the modiolar research array—multi-centre collaborative study in human temporal bones", Cochlear Implants Int. Aug. 12, 2011(3) pp. 129-139, PMCID: PMC3159433.

Coulson et al., "An autonomous surgical robot for drilling a cochleostomy: preliminary porcine trial", Clin Otolaryngol, vol. 33-4, pp. 343-347, Aug. 2008.

Coulson et al., "ENT challenges at the small scale", Int J Med Robot, vol. 3- 2, pp. 91-96, Jun. 2007.

Gomez-Blanco et al., "Intraoperative tremor monitoring for vitreoretinal microsurgery", in *Proc. Medicine Meets Virtual Reality 8*, 2000, pp. 99-101.

Han et al., "Common path optical coherence tomography with fibre bundle probe", *Electronics Letters*, vol. 45-22, pp. 1110-1112, Oct. 2009 NIHMSID 188391.

Iordachita et al., "Steady-Hand Manipulator for Retinal Surgery", in *MICCAI Workshop on Medical Robotics*, Copenhagen, 2006, pp. 66-73.

Labadie et al., "Clinical Validation Study of Percutaneous Cochlear Access Using Patient Customized Micro-Stereotactic Frames", Otol. Neurotol, vol. 31-1, pp. 94-99, Jan. 2010, PMC2845321.

MacLachlan et al., "High-speed microscale optical tracking using digital frequency-domain multiplexing", *IEEE Trans Instrum Meas*, vol. 58, No. 6, Jun. 2009, pp. 1991-2001.

MacLachlan et al., "Optical tracking for performance testing of microsurgical instruments", Robotics Institute, Carnegie Mellon University CMU-RI-TR-07-01, Jan. 2007, pp. 15.

Majdani et al., "Force measurement of insertion of cochlear implant electrode arrays in vitro: comparison of surgeon to automated insertion tool", Acta Oto-Laryngologica, vol. 130-1, pp. 31-36, Jan 2010. <Go to ISI>://000274416300005Doi 10.3109/00016480902998281.

Niparko, "Chapter 3: Cochlear Implants: Clinical Applications", Zeng (ed.), *Cochlear Implants: Auditory Prostheses and Electric Hearing*, New York, Springer, 2004, pp. 53-100.

Rau et al., "Automated insertion of preformed cochlear implant electrodes: evaluation of curling behaviour and insertion forces on an artificial cochlear model", Int Comput Assist Radio Surg, vol. 5-2, pp. 173-181, Mar. 2010.

Riviere et al., "A study of instrument motion in retinal microsurgery", in *Proc. 21st Annu. Conf. IEEE Eng. Med. Biol. Soc.*, Chicago, 2000.

Rothbaum et al., "Robot-assisted stapedotomy: micropick fenestration of the stapes footplate", Otolaryngology—Head and Neck Surgery, vol. 127-5, pp. 417-426, Nov. 2002.

Rothbaum et al., "Task Performance in stapedotomy: Comparison between surgeons of different experience levels", Otolaryngology—Head and Neck Surgery, vol. 128-1, pp. 71-77, Jan. 2003.

Schurzig et al., "A force sensing robot for cochlear electrode implantation", in IEEE International Conference on Robotics and Automation, May 3-8, 2010, pp. 3674-3679.

Taylor et al., "A Steady-Hand Robotic System for Microsurgical Augmentation", International Journal of Robotics Research, vol. 18-12, 1999.

Taylor et al., "An Image-directed Robotic System for Precise Orthopaedic Surgery", *IEEE Transactions on Robotics and Automation*, vol. 10-3, pp. 261-275, 1994.

Tucci, et al., "Chapter 13: Medical and Surgical Aspects of Cochlear Implantation", Niparko (ed), *Cochlear Implants: Principles & Practices 2nd Edition*, Philadelphia, Lippincott, Williams & Wilkins, 2009, pp. 161-186.

Uneri et al., "New Steady-Hand Eye Robot with Microforce Sensing for Vitreoretinal Surgery Research", in BIOROB Conference, Tokyo, Sep. 26-29, 2010, pp. 814-819.

Zhang et al., "A pilot study of robot-assisted cochlear implant surgery using steerable electrode arrays", Med Image Comput Comput Assist Interv, vol. 9-Pt 1,pp. 33-40, 2006.

Zhang et al., "Inroads Toward Robot-Assisted Cochlear Implant Surgery Using Steerable Electrode Arrays", Otology and Neurotology, p. In Press; Published ahead of print, 2010, pp. 1199-1206 10.1097/MA0.0b013e3181e7117e.

Zhang et al., "Path planning and workspace determination for robot-assisted insertion of steerable electrode arrays for cochlear implant surgery", Med Image Comput Comput Assist Interv, vol. 11-Pt 2, pp. 692-700, 2008.

\* cited by examiner

METHOD AND APPARATUS FOR COCHLEAR IMPLANT SURGERY

CROSS-REFERENCE OF RELATED APPLICATION

This application claims priority to U.S. Provisional Application No. 61/384,940 filed Sep. 21, 2010, the entire contents of which are hereby incorporated by reference.

BACKGROUND

1. Field of Invention

The field of the currently claimed embodiments of this invention relates to systems, devices and methods for cochlear implant surgery.

2. Discussion of Related Art

Many different types of Cochlear implant surgery (J. Niparko (ed), *Cochlear Implants: Principles & Practices*, Philadelphia, Lippincott, Williams & Wilkins, 2009; D. Tucci and T, Pilkington, "Medical and surgical aspects of cochlear implantation". in *Cochlear Implants: Principles & Practices*, J. K. Niparko, Ed, Philadelphia: Lippincott, Williams & Wilkins, 2009) can be of immense auditory, linguistic and developmental benefit to patients with severe hearing loss due to the loss of hair cell transduction within the cochlea. Estimates from the National Institute of Deafness and Other Communication Disorders (NIDCD) are that approximately 188,000 people worldwide have received implants ("Statistics about Hearing, Balance, Ear Infections, and Deafness," http://wwvv.nidcd.nih.gov/health/statistics/hearing.asp#1, 2010) and that rates of applying electrified implants to the ear are accelerating.

The surgical procedure is potentially complicated by difficulties with implant electrode array insertion (e.g., C. J, Coulson, A. P. Reid, D. W. Proops, and P. N. Brett, "ENT challenges at the small scale", Int J Med Robot, vol. 3-2, pp. 91-6, June 2007. http://www.ncbi.nlm,n1h,gov/entrez/query fcgi?cmd=Retrieve&db=PubMed& dopt=Citation&list uids=17619240 10.1002/rcs.132) and serious complications may occur. One particularly challenging step is the actual insertion of the implant into the cochlea (see, e.g., FIGS. 1A-1C). After accessing the scala tympani (via direct round window insertion, or drilling open a cochleostomy to gain access to the cochlea) an electrode array is inserted into scala tympani of the cochlea. Several designs of cochlear implant arrays have relied on stylet-based insertion techniques. The Advanced Bionics arrays used in ca. 2003-2006 used a pre-curved array that was loaded onto a hand-held insertion tool. Once inserted into the scala tympani, the insertion tool was used to guide the array into the proximal 3 mm of the scala and then advance the array off of the rigid stylet into the first turn of the cochlea, allowing the curvature of the silastic carrier to find the proper trajectory through the turn. Here, if the stylet based on the hand-held tool were to be advanced too far into the cochlea, contact forces generated can damage the cochlea.

Over the past 6 years, the Cochlear Corporation Freedom and C512 arrays have used a stylet-based strategy: A stylet is used to hold the implant straight while it is inserted to a desired depth into the cochlea. The array is advanced over the stylet, which is held in a fixed position. The implant array then naturally curves to follow the cochlea given it's memory as a curved array once off of the stylet. The stylet is then withdrawn. If the stylet and implant are advanced too far into the cochlea, the resulting contact forces can damage the cochlea either due to direct impact or buckling of more proximal aspects of the carrier. Research also has been reported in which a sheath-style insertion device is used to perform the same function as a stylet in holding the implant straight while it is inserted to a desired depth into the cochlea. The implant array naturally curves to follow the cochlea as it is deployed further through the sheath. One example of such a sheath is the Modiolar Research Array (R. Briggs et al., "Development and evaluation of the modiolar research array—multi-centre collaborative study in human temporal bones", Cochlear Implants Int. 2011 August 12(3) pp 129-139, PMCID: PMC3159433). Again, if the stylet and implant are advanced too far into the cochlea, the resulting contact forces can damage the cochlea either due to direct impact or buckling of more proximal aspects of the carrier.

Many other array designs used both historically and presently present a potential problem with substantial growth in resistance as the array is inserted beyond 12 mm (Tucci, et al.), with consequent risks to the integrity of intracochlear membranous structures (FIG. 2).

Several approaches to providing guidance or assistance in avoiding damage to the cochlea during implant insertion have been reported recently. Labadie et al. report a microstereotactic device for aligning an implant array with the cochlea for percutaneous insertion based on preoperative images (R. F. Labadie, R. Balachandran, J. Mitchell, J. H. Noble, O. Majdani, D. Haynes, M. Bennett, B. M. Dawant, and M. Fitzpatrick, "Clinical Validation Study of Percutaneous Cochlear Access Using Patient Customized Micro-Stereotactic Frames", Otol. Neurotol, vol. 31-1, pp. 94-99, 2010, PMC2845321). Schurzig, Labadie, and Webster report a system that combines an "active canula" robot with delicate force sensing capabilities to sense contact between the implant and the cochlea (D. Schurzig, R. F. Labadie, and R. J. Webster, "A force sensing robot for cochlear electrode implantation", in IEEE International Conference on Robotics and Automation, 2010, pp. 3674-3679), using a force sensor incorporated into the robotic mechanism that advances the implant into the cochlea, Rau et al. (T. S. Rau, A. Hussong, M. Leinung, T. Lenarz, and O. Majdani, "Automated insertion of preformed cochlear implant electrodes: evaluation of curling behaviour and insertion forces on an artificial cochlear model", Int Comput Assist Radio! Surg, vol. 5-2, pp. 173-81, March 2010.http://www,ncbi,nlm.nih'govientrez/query. fcgi?cmd=Retrieve&db=PubMed&dopt=Citation&list uids=20033522 10,1007/s11548-009-0299-9) have also proposed a robotic cochlear insertion device and have reported phantom studies of insertion forces using a load cell attached to the insertion mechanism. Zhang, Simaan, et al. have developed an actively deforming, steerable, cochlear implant that curves to follow the cochlea during insertion (J. Zhang, W. Wei, S, Manolidis, J. T. Roland, Jr., and N. Simaan, "Path planning and workspace determination for robot-assisted insertion of steerable electrode arrays for cochlear implant surgery", Med Image Comput Comput Assist Interv, vol. 11-Pt 2, pp. 692-700, 2008.http://www.ncbi,nlm.nih.gov/entrez/query.fcgi?cmd=Retrieve&db=PubMed & dopt=Citation&list uids=18982665; J. Zhang, K, Xu, N. Simaan, and S. Manolidis, "A pilot study of robot-assisted cochlear implant surgery using steerable electrode arrays", Med Image Comput Comput Assist Interv, vol. 9-Pt 1, pp. 33-40, 2006. http://www.ncbi.nlm,nih.zov/entrez/ querylegi?cmd=Retrieve&db=PubMed& dopt=Citation&list uids=17354871; J. Zhang, W. Wei, J. Ding, J. T. Roland, S. Manolidis, and N. Simaan, "Inroads Toward Robot-Assisted Cochlear Implant Surgery Using Steerable Electrode Arrays", Otology and Neurotology, p. in Press; Published ahead of print, 2010 10.1097/ MA0.0b013e3181e7117e). They report experiments using a load cell mounted on their robotic manipulation device. Some limitations of these systems include reliance on a fairly large and cumbersome robotic insertion tool and the necessity to implement an extremely delicate force sensing mechanism. In the case of the reported systems, the difficulty is exacerbated by the moving mass of the mechanism distal to the force sensor and possible friction forces.

Other authors (e.g., C. J. Coulson, R. P. Taylor, A. P. Reid, M, V. Griffiths, D. W. Proops, and P. N. Brett, "An autonomous surgical robot for drilling a cochleostomy: preliminary porcine trial", Clin Otolaryngol, vol. 33-4, pp. 343-7, August 2008. http://www.ncbi,n1m.nih.gov/entrez/query.fcgi?cmd=Retrieve&db=PubMed&dopt=Citation&list uids=18983344C0A1703 [pii] 10.1111/j.1749-4486.2008.01703.x; O. Majdani, D, Schurzig, A. Hussong, T. Rau, I. Wittkopf, T. Lenarz, and R. F. Labadie, "Force measurement of insertion of cochlear implant electrode arrays in vitro: comparison of surgeon to automated insertion tool", Acta Oto-Laryngologica, vol. 130-1, pp. 31-36, January 2010. <Go to ISI>:// 000274416300005Doi 10.3109/00016480902998281) have proposed robotic devices to assist in drilling the skull to gain access to the cochlea for implant insertion. These systems do not address the problem of inserting an implant without damage to the cochlea.

Skilled otologic surgeons have the manual dexterity and steadiness to insert implants without damage to the cochlea. What they lack is feedback to know when the implant or stylet has been introduced too far into the cochlea. In his review article (C. J, Coulson, et al, id), C. J. Coulson states:

If the surgeon were able to visualize or 'feel' forces imparted on the electrode array and then guide the array around the path of least resistance, he/she would be able to place the electrode whilst minimizing the trauma to the cochlea.

Coulson further suggests an endoscopic "flexible digit with visualization (the scala tympani being about 1 mm$^2$ in cross-section) would allow the tip to be manoeuvred through the hollow portion of the scala tympani", but discloses no feasible way to implement such a device, which he describes as being "technically very difficult" since it would require both a light source and a visualization device in a tiny space. As an alternative, he suggests:

Another potential solution would be to fit the electrode array with sensing elements at the tip, which could feed back onto a monitor, informing the surgeon whether the tip was against the solid outer cochlear wall or in the middle of the hollow scalatympani.

However, he does not disclose any feasible means for performing such sensing and implies that he is interested only in contact/noncontact sensing. Some implant manufacturers (e.g., Cochlear Corp) place fiducial marks along the implant to assist the surgeon in determining how deep the implant has been inserted into the cochlea and, hence, how much further it can be inserted before it comes into contact with the cochlear wall at the start of the "turn" into the high curvature portion of the cochlea. One limitation of this approach is that the surgeon has no clearly defined reference for relating the fiducial marks to the highly variable position of the opening in the cochlea. Similarly, the surgeon lacks a patient-specific measurement giving the exact depth of insertion required. There thus remains a need for improved systems, devices and methods for cochlear implant surgery.

SUMMARY

A system for cochlear implant surgery according to some embodiments of the current invention includes a reference device having at least a portion adapted to be arranged at a fixed position relative to a cochlea of a patient to provide a reference position, an image acquisition and processing system adapted to acquire an image of at least a portion of the cochlea relative to the reference position and to provide an implant plan based at least partially on the acquired image, and an implant system adapted for implanting a cochlear lead array using the reference position and the implant plan.

A reference device according to some embodiments of the current invention includes a spring structure such that the reference device has a size and shape to be insertable into and removable from an opening made during at least one of a cochleostomy or mastoidectomy surgical procedure while the spring structure is in a compressed configuration and the reference device is fixed in position while the spring structure is in a restored configuration.

A method of surgically implanting a prosthetic device in a patient's cochlea according to some embodiments of the current invention includes providing a fiducial reference at a spatially fixed position relative to the patient's cochlea, acquiring an image of at least a portion of the patient's cochlea relative to the fiducial reference, processing the image to determine a surgical implant plan, and providing results of the surgical implant plan for a surgeon to implant at least a portion of the prosthetic device using the implant plan and the fiducial reference.

BRIEF DESCRIPTION OF THE DRAWINGS

Further objectives and advantages will become apparent from a consideration of the description, drawings, and examples.

DETAILED DESCRIPTION

Figure 1A:
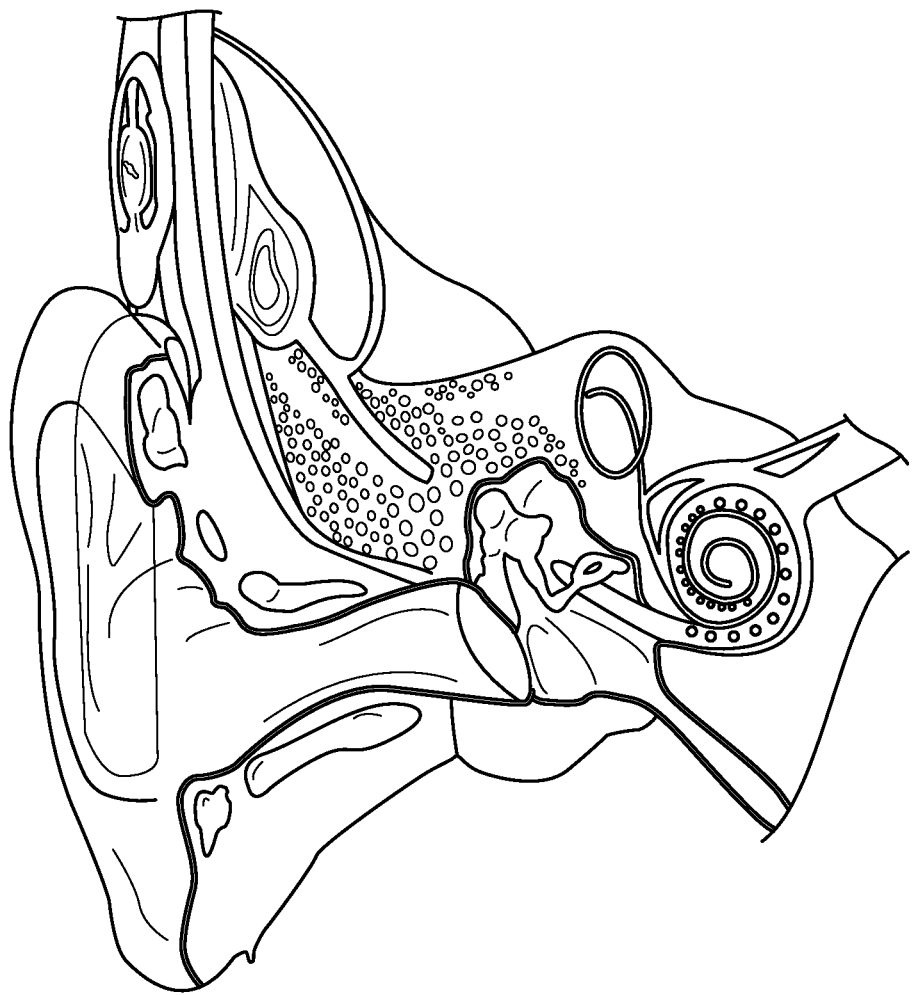
FIGS. 1A-1C illustrate a cochlear implant and cochlear implant surgery.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention provide systems, methods and associated devices for avoiding damage to the cochlea during implant insertion. In R. H. Taylor, J. U. Kang, and J. Niparko, "Optical Sensing System for Cochlear Implant Surgery", The Johns Hopkins University, U.S. Provisional Patent Application No. 61/384,934, filed on Sep. 21, 2010, the entire contents of which are incorporated herein by reference, some of the current inventors disclosed multiple embodiments in which fiber-optical OCT sensors are embedded into a cochlear implant or insertion device such as a stylet to provide a direct measurement of the implant-to-cochlea geometric relationship during the insertion process. It will be readily understood that these embodiments may be adapted by one of ordinary skill in the art to be used with another insertion device such as a sheath. The methods and apparatus disclosed in that case provided an approach for addressing the problem of determining whether the stylet tip or, alternatively, the end of the implant is in contact with the cochlea or in the middle of the hollow scala tympani. Further, it provided feedback to the surgeon informing him or her of the distance by which either the stylet or implant may be advanced before contact occurs. It will be readily understood that these methods may be adapted by one of ordinary skill in the art to be used with another insertion device such as a sheath.

Some embodiments of the current invention provide an alternative approach using an indirect measurement of insertion depth into the cochlea. This is important information that the surgeon requires to avoid damaging the cochlea. Methods, systems and associated devices according to some embodiments of the current invention are readily adaptable to many implant designs and alternative embodiments. An aspect of some embodiments of the current invention is that they do not require a robot or other elaborate mechanical apparatus that could prove difficult to introduce into surgery. However, embodiments of the current invention are compatible with robotic or other mechanical insertion aids and some embodiments can include a robot or similar device. The information provided by some embodiments of the current invention can also significantly improve the effectiveness of a variety of technical aids for the insertion process (including robotic devices or mechanical aids for adjusting the curvature or shape of the implant). However, many embodiments of the current invention do not require a robot or other elaborate supporting apparatus or adjuncts that may prove difficult to introduce into routine clinical practice, although the basic invention is compatible with robotic aids and other embodiments may include a robot.

Some embodiments of the current invention provide an approach for addressing the problem of determining whether the insertion device (e.g. stylet or sheath) tip or, alternatively, the end of the implant is in contact with the cochlea or in the middle of the hollow scala tympani. Further, some embodiments of the current invention can provide feedback to the surgeon informing him or her of the distance by which either the insertion device or implant may be advanced before contact occurs. This can be crucial information that the surgeon requires to avoid damaging the cochlea.

Further, since the information can provide real-time information about the position of the implant in the cochlea, it may be adapted readily to work with multiple implant designs or to improve the effectiveness of a variety of technical aids for the insertion process (including robotic devices or mechanical aids for adjusting the curvature or shape of the implant).

Figure 3:
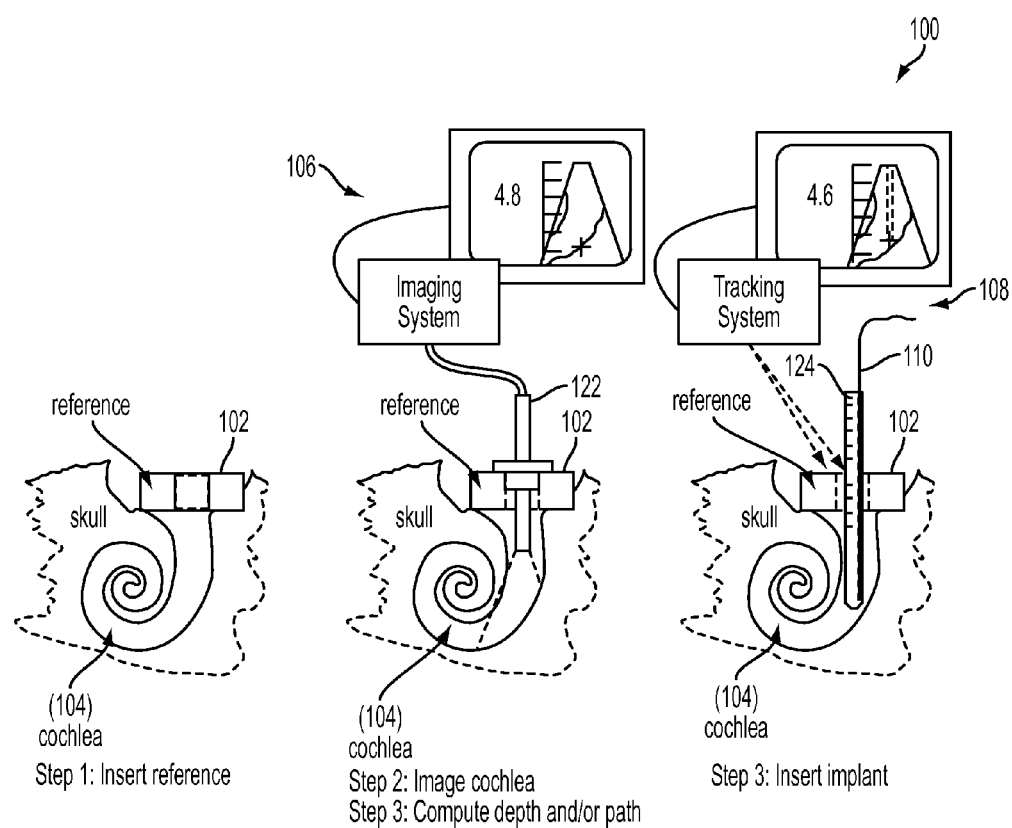
FIG. 3 is a schematic illustration of a system, method and associated devices for cochlear implant surgery according to an embodiment of the current invention.

FIG. 3 provides a schematic illustration of a system for cochlear implant surgery 100 according to an embodiment of the current invention. The system for cochlear implant surgery 100 includes a reference device 102 having at least a portion adapted to be arranged at a fixed position relative to a cochlea 104 of a patient to provide a reference position. The system for cochlear implant surgery 100 also includes an image acquisition and processing system 106 adapted to acquire an image of at least a portion of the cochlea 104 relative to the reference position and to provide an implant plan based at least partially on the acquired image. The system for cochlear implant surgery 100 further includes an implant system 108 adapted for implanting a cochlear lead array 110 using the reference position and the implant plan.

Figure 4:
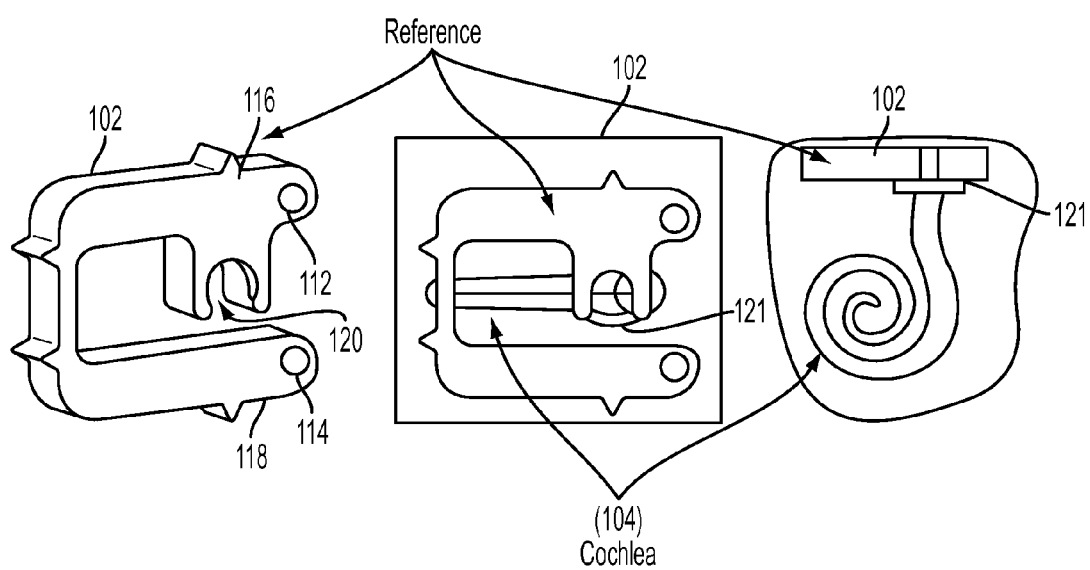
FIG. 4 is an illustration of a reference device according to an embodiment of the current invention.

According to some embodiments of the current invention, the reference device 102 is structured to be fixable to and removable from the patient during surgery. For example, the reference device 102 can be, but is not limited to, a spring-clip reference device that is insertable into an opening made during at least one of a cochleostomy or mastoidectomy surgical procedure and reconfigurable to remain fixed during a cochlear implant procedure. FIG. 4 shows a more detailed view of an embodiment of the reference device 102 in which it is a spring-clip reference device. In this embodiment, the reference device 102 has indents 112, 114 defined by opposing spring members 116 and 118, respectively, that are suitable to receive a tool for compressing the spring members 116 and 118 towards each other for inserting into and removing from the surgical opening. The reference device 102 further defines a slot 120 that is suitable to provide a guide for an imaging probe and/or a surgical device such as a stylet or sheath for implanting an electrode array. The slot 120 is suitable to be aligned with the opening 121 in the cochlea.

According to some embodiments of the current invention, the image acquisition and processing system 106 can include an imaging probe 122. The imaging probe 122 can be, but is not limited to, an optical coherence tomography (OCT) imaging probe. In another embodiment, the imaging probe 122 can be an ultrasound imaging probe, for example.

The image acquisition and processing system 106 can include one or more data processors, memory devices and data storage devices. For example, the image acquisition and processing system 106 can include a computer or a network of computers, such as, but not limited to, hand-held, tablet, laptop, personal, or workstation computers. The image acquisition and processing system 106 can also include one or more display devices and/or feeds into other peripheral devices. According to an embodiment of the current invention, the image acquisition and processing system 106 can be configured to provide a three-dimensional image of at least part of an insertion area of the cochlea 104. According to an embodiment of the current invention, the image acquisition and processing system 106 can be configured to provide at least one distance measurement from the imaging probe 122 to a portion of the cochlea 104. According to an embodiment of the current invention, the image acquisition and processing system 106 can be configured to provide a plurality of distance measurements from the imaging probe 122 to portions of the cochlea 104.

According to some embodiments of the current invention, the image acquisition and processing system 106 can include an external imaging system. The external imaging system can be, but is not limited to, a cone-beam x-ray system, a computed tomography x-ray system, and/or a magnetic resonance imaging (MRI) system.

In operation, the surgeon arranges the reference device 102 such that it remains fixed relative to the patient's cochlea 104. For example, in one embodiment, the reference device 102 is a spring-clip reference device. The surgeon can use a tool to compress the spring members 166, 188 such that it is insertable into an opening made during at least one of a cochleostomy or mastoidectomy. The reference device 102 can have structural features, such as teeth in the example of FIG. 4, to help it remain stable in place during the implant procedure. An imaging device, such as, but not limited town OCT probe, can be inserted into slot 120 defined by the reference device 102 such that it has a defined position relative to the reference device 102. The imaging probe can be used to obtain at least one distance measurement to a portion of the cochlea 104. If desired, the imaging probe can be used to obtain a plurality of distance measurements to portions of the cochlea 104, or even to obtain a three-dimensional map of a portion or substantially the entire cochlea 104.

The image acquisition and processing system 106 can also be configured, for example by being programmed, to provide a plan to the surgeon for the cochlear implant surgery. The plan can be as simple as providing a distance value to the surgeon corresponding to the first sharp bend in the cochlea, for example, but it is not limited to only this example. In other cases, the plan can be more complex, such as, but not limited to, a detailed scale image and planned path. In one example, the surgeon can use an insertion device such as a stylet or sheath to implant a lead array using the plan to know how deeply to insert the stylet or sheath. After the lead array is implanted, the surgeon can use the tool to compress the reference device 102 to remove it.

The following describes one possible embodiment in more detail. The broad concepts of the current invention should not be construed as being limited to this particular example. FIG. 3 is also useful for describing an embodiment of a method according to the current invention. The insertion according to this embodiment method comprises the following:

1. Placement of a reference fiducial object at or near the opening of the cochlea after the cochleostomy is performed. The detailed design of the fiducial will depend on the specific choice of imaging and feedback to be provided in Steps 2 and 4, below. Two important general characteristics are a) that it be able to be placed firmly onto the patient's skull so that it provides a stable reference during Steps 2 and 4 and that it be able to be removed after insertion without disturbing the implant.
2. Imaging of the cochlea relative to the reference fiducial object.
3. Using the image data to plan an insertion path or insertion depth relative to the reference fiducial object.
4. Insertion of the implant into the cochlea while providing the surgeon with information about the position, orientation, or depth of insertion of the implant relative to the reference fiducial object.

The reference object may then be removed and surgery may proceed normally. There are many possible specific embodiments for each step. We will discuss these in subsequent sections.

Step 1: Placement of Reference Object At or Near the Opening of the Cochlea

The key requirements of the reference object are 1) that it can be firmly placed onto the patient's skull during imaging and insertion so that its position relative to the cochlea is the same during imaging (Step 2) and insertion (Step 3); 2) that it provide a suitable reference for imaging so that its position relative to the images is known; and 3) that it also provide a suitable reference during insertion so that the position of the distal end of the cochlear implant relative to the implant may be determined.

Figure 5:
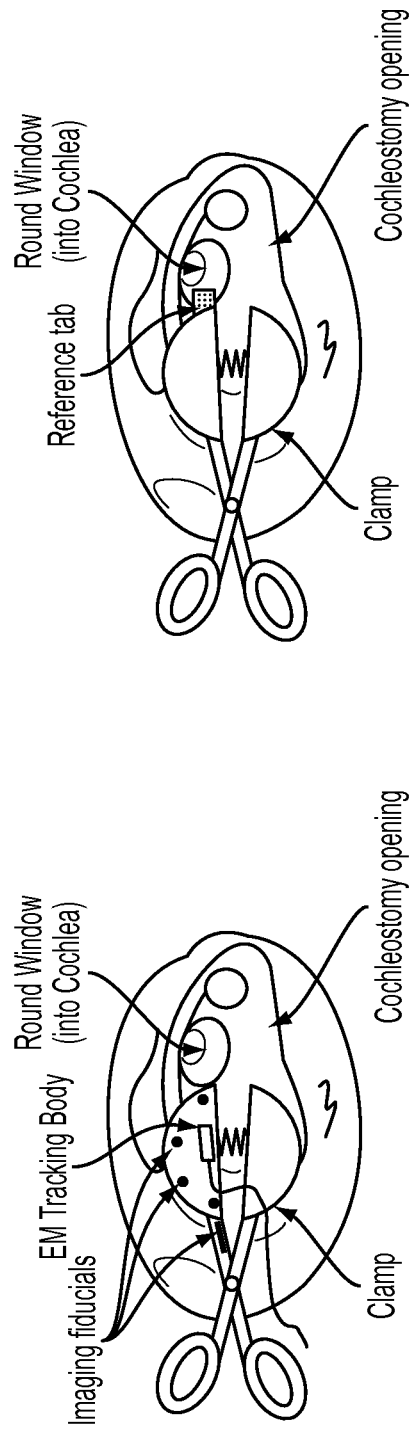
FIG. 5 is an illustration of further reference devices according to embodiments of the current invention.

FIG. 5 shows two possible embodiments of the reference object, in which a spring-loaded mechanical clamp holds the fiducial object firmly against the sides of the hole made into the skull for the cochleostomy or the mastoidectomy made to obtain access for the cochleostomy. However, it will be readily appreciated that other means may be used to secure the fiducial object to the skull. Similarly, although FIG. 5 shows a fiducial object of approximately the same size as the cochleostomy or mastoidectomy opening, this is not required in all embodiments of the invention. The fiducial may extend beyond the opening if necessary to provide more accurate referencing, although it is important that the design not interfere with the surgeon's ability to introduce the implant into the cochlea. The fiducial object may comprise one or more reference surfaces to assist in positioning of imaging probes in a known position relative to the cochlea and in measuring the insertion of the insertion depth of the implant relative to the cochlea. Similarly, it may comprise additional tracking devices or fiducials, such as electromagnetic (EM) tracker coils or optical tracker markers that may be used to track the pose of the reference object relative to imaging probes or implant insertion tools. It may also comprise specialized fiducial marks to assist in locating the fiducial reference relative to x-ray tomographic images of the skull and cochlea or in video tracking of probes and insertion tools relative to the reference.

FIG. 4 shows one possible embodiment for a spring-clip fiducial for inserting into the opening made during the cochleostomy or mastoidectomy. In this case, two triangular "teeth" grasp the sides of the opening when the reference body is in place, thus holding it in place. Two holes are provided for a tool to grasp the implant and compress the spring during insertion. A slotted tab provides a spatial reference for imaging and insertion into the cochlea. The slot permits removal of the reference without threading it out over the implant after insertion.

There are a number of commercial EM tracking systems for medical applications, including systems manufactured by Ascension Technologies and Northern Digital, Incorporated. These systems use an electromagnetic field generation unit, together with small detector coils that may be built into surgical instruments and devices. The tracking system measure either 5 Degrees-of-Freedom (5 DoF), i.e., 3 translational DoF+2 orientation DoF, or 6 DoF, i.e., 3 translational DoF and 3 rotational DoF, of the coils relative to the field generator. Multiple coils may be affixed to or embedded in a single rigid object to improve the overall accuracy of measurement or to provide a 6 DoF measurement if only 5 DoF coils are available. The mathematics associated with use of such tracking systems are well known in the art. Briefly, if $F_{br}$ represents the measured 6 DoF pose of the reference fiducial relative to the field generation unit (i.e., the coordinate transformation between fiducial reference coordinates and field generator coordinates) and $F_{bt}$ represents the measured 6 DoF pose of a tool or probe relative to the field generation unit, then the 6 DoF pose of the tool relative to the reference object is given by $F_{rt} = F^{-1}_{br} F_{bt}$. It is usually important to put the reference object as close as possible to the tool or probe being tracked without interfering with the surgical task, in order to reduce the effects of errors in measuring orientation of the tracked coils and of various non-linearities and distortions in the measurement systems. Most surgical tracking systems are designed to be used in a fairly large work volume. If necessary, it may be desirable to construct a specialized EM tracking system with a much smaller work volume, appropriate for this application, but with higher accuracy within the measurement volume. In this case, one option might be to build field generation coils into the fiducial object itself. Alternatively, the field generator may possibly be mounted onto the head holder used to clamp the skull in surgery or may be placed on or near the patient's head.

Similarly, there are many commercial optical tracking systems for surgery, such as the Optotrak or Polaris systems manufactured by Northern Digital Incorporated or Claron Technology's MicronTracker system. Similarly, there are many research systems, such as the optical tracking systems developed at CMU by Riviere et al. for study of microsurgical instrument motion. See, for example:

M. A. Gomez-Blanco, C. N. Riviere, and P. K. Khosla, "Intraoperative tremor monitoring for vitreoretinal microsurgery", in *Proc. Medicine Meets Virtual Reality 8*, 2000, pp. 99-101

C. N. Riviere and P. S. Jensen, "A study of instrument motion in retinal microsurgery", in *Proc. 21st Annu. Conf IEEE Eng. Med. Biol. Soc.*, Chicago, 2000

R. MacLachlan and C. Riviere, "Optical tracking for performance testing of microsurgical instruments", Robotics Institute, Carnegie Mellon University CMU-RI-TR-07-01, 2007.

R. MacLachlan and C. Riviere, "High-speed microscale optical tracking using digital frequency-domain multiplexing", *EEE Trans Instrum Meas*, p. submitted, 2007.

Typically, these systems track the position of markers in multiple cameras or imaging detectors whose relative poses are known and rely on triangulation to determine 3D positions of the markers and 6 DoF poses of constellations of markers relative to the cameras. Once poses are known, the mathematical methods of using them to track relative poses of multiple objects are similar to the methods used with EM trackers. The markers may be "active" light emitting devices such as LEDs or passive reflectors. Similarly, more general computer vision methods known in the art may be used to track the relative 6 DoF pose of multiple objects. The accuracy of any of these optical methods depends on the resolution of the image detectors, the field of view, mechanical construction of the system, and accuracy of calibration. For the imaging volumes required for this application, it is relatively straightforward to produce custom systems with a few 10's of microns precision, more than sufficient for this application, One advantage of EM systems is that they are not subject to line-of-sight restrictions. Optical systems are typically more accurate, but it is necessary to ensure that there is a clear line of sight between the cameras and the tracked markers.

Step 2: Imaging of the Cochlea Relative to the Reference Device

Several systems may be used to obtain 3D images of the cochlea. Broadly, these fall into two classes:

1. Imaging Probe Methods: An imaging probe may be placed at the cochlear opening or inserted a short distance into the opening of the cochlea, but not so far as to risk the probe coming into contact with the cochlear wall. Several imaging technologies may be used to produce 3D images of the cochlea beyond the end of the probe. One such imaging technology is 3D optical coherence technology (3DOCT). In one embodiment, such a probe would be a 3D Fourier Domain Common Path OCT probe similar to that demonstrated by Kang et al (J.-H. Han, X. Liu, C. G. Song, and J. U. Kang, "vol. 45, no, 22, pp., October, 2009 "Common path optical coherence tomography with fibre bundle probe", *Electronics Letters"* vol. 45-22, pp. 1110-1112, October 2009 NIHMSID 188391). In another embodiment, the probe may be an ultrasound-imaging probe. Typically, the probe may only be able to produce an image of the cochlea only as far as the point where it turns into its tight spiral. In this case, the system and method may still be used to identify the point at which the implant must begin to coil into the cochlea. However, it may also be possible, especially with high frequency ultrasound, to image several turns into the cochlea. In this case, additional guidance assistance may be possible.

Several methods may be provided to determine the necessary coordinate transformation $F_{rc}$ relating the cochlear image coordinates to the coordinate system associated with the reference device. One straightforward method would be to bring a reference surface or fiducial mark on the probe into contact or close proximity with a reference surface or fiducial mark on the reference device prior to imaging. In this case, it will be necessary for the probe to be capable of imaging into the cochlea when this relationship is achieved. An alternative would be to use a tracking technology such as the optical or EM trackers discussed in Step 1 to measure the pose $F_{rp}$, of the probe relative to the reference fiducial. A suitable calibration method, well known to those of ordinary skill in the art, may be used to determine the transformation $F_{rc}$ between probe and image coordinates, and $F_{rc}$ may be computed from $F_{rc}=F_{rp}F_{pc}$.

2. Tomographic x-ray imaging: Intraoperative x-ray tomography may be used to provide high resolution 3D volumetric images of the cochlea. Although conventional CT scanners may possibly be used, high resolution "flat panel" C-arm systems providing "cone-beam" 3D reconstructions are preferred for this intraoperative application. Modern cone beam systems can readily produce image resolutions on the order of 100 microns for the head and neck, which is sufficient for current purposes. In this case, fiducial markers on the reference device and visible in x-rays, together with other portions of the tool itself, may be located in the reconstructed 3D image, and this information may be used to determine the transformation $F_{rc}$ relating the cochlear image coordinates to the coordinate system associated with the reference fiducial.

Step 3: Using the Image Data to Determine a Desired Depth or Path of the Implant Relative to the Reference Device Once the 3D image of the cochlea in obtained, suitable computer software may be used to display the 3D image or selected 2D slices of the 3D image for the surgeon to examine. These images may be used by the surgeon for planning an insertion path and depth of the implant into the cochlea, relative to the reference object. Computer image processing and/or computer graphics may be used as part of this assistance process. For example, the computer may use image processing to determine boundary surfaces in the cochlear image. Similarly, it may display computer graphic overlays of the implant at various insertion points into the cochlea. Such graphic displays of the implant, image and reference object may be shown in "image" or "reference object" coordinates. Likewise it may compute desired insertion depth of the implant or of some known point of the implant relative to the reference object or relative to some fiducial surface or mark on the reference object. It is important to note that this planning may, be done intraoperatively. Further, it may be extremely simple. For example, it may consist simply of computing a desired insertion depth from the images or just of displaying the images on a computer display. Further, the computer display may be a conventional display or may be an "image injection" display such as found in some operating microscopes, in which the surgeon can see the displayed information while observing the surgical field through the microscope.

Step 4: Insertion of the Implant

Several possible means may be used to assist the surgeon in monitoring or controlling the insertion depth of the implant into the cochlea:

1. The most straightforward methods would rely on the surgeon's natural hand-eye coordination. The planning done in Step 3 would include determining a desired relative position of a reference surface or feature on the reference device to a reference feature (such as a mark) on the implant. The surgeon would then insert the implant until this point is reached, at which point the end of the implant would be just at the place where it is supposed to begin turning into the spiral. In one embodiment, index marks might be placed at regular intervals (e.g., every millimeter) along the implant and the surgeon would be told to insert the implant until a particular index mark or fractional position (e.g., "5.2 mm") is reached. An advantage of these methods is that they require minimal hardware, although they may be less accurate or convenient than some of the other methods described above.

2. A tracking system or device may be used to track the position and orientation of the implant relative to the reference device during insertion and suitable feedback may be provided to the surgeon to provide assistance during insertion:

For tracking the implant relative to the reference device, a computer vision system may be used, possibly with additional visible marks placed on the reference object and/or the implant. Alternatively, a marker-based tracking system such as the optical or EM tracking systems discussed in Step 1 may be used to track a tool used to hold the implant, relative to the reference device. If a tool is used, it would be used to grasp the implant in a known position relative to the tool. Alternatively, this position may be measured after the implant is grasped by touching the end of the implant to known reference surfaces on the reference device while the tool is tracked. Alternatively, an additional tracking fiducial may be incorporated into a device that holds the implant in a known position and orientation at the time the tracked tool is used to grasp the implant.

For providing feedback to the surgeon during insertion, a number of methods known in the surgical assistance art may be used, either alone or in combination. For example, a computer display may show a graphic indication of the implant tip position or implant structure superimposed on the images obtained in Step 2. It may display numerical information showing how deeply the implant has been inserted into the cochlea or how far it still has to travel before it reaches the cochlear turn. Similarly, this information may be provided by synthesized speech. Other "auditory sensory substitution" methods (e.g., P. K. Gupta, A Method to Enhance Microsurgical Tactile Perception and Performance Through the Use of Auditory Sensory Perception, thesis in M. S. in Engineering, The Johns Hopkins University, Baltimore, 2001; M. Balicki, A. Uneri, I. Iordachita, J. Handa, P. Gehlbach, and R. H. Taylor, "Micro-force Sensing in Robot Assisted Membrane Peeling for Vitreoretinal Surgery", in Medical Image Computing and Computer-Assisted Intervention (MICCAI), Beijing, September 2010, p. to appear) may be used to provide warning when the implant is approaching the cortical turn and should not be advanced further.

Robotic assistance methods may also be used to reduce the surgeon's hand tremor and provide additional manipulation constraints. For example, the cooperatively-controlled Johns Hopkins "Steady Hand" robots (e.g., R. H. Taylor, P. Jensen, L. L. Whitcomb, A. Barnes, R. Kumar, D. Stoianovici, P. Gupta, Z. X. Wang, E. deJuan, and L. R. Kavoussi, "A Steady-Hand Robotic System for Microsurgical Augmentation", International Journal of Robotics Research, vol. 18-12, 1999; P. J. Berkelman, D. L. Rothbaum, J. Roy, Sam Lang, L, L. Whitcomb, G. Hager, P. S. Jensen, R. H. Taylor, and J. Niparko, "Performance Evaluation of a Cooperative Manipulation Microsurgical Assistant Robot Applied to Stapedotomy", in Medical Image Computing and Computer-Assisted Interventions (MICCAI 2001), Utrecht, 2001, pp. 14264429; D. L. Rothbaum, J. Roy, P. Berkelman, G. Hager, D. Stoianovici, R. H. Taylor, L. L. Whitcomb, M. Howard Francis, and J. K. Niparko, "Robot-assisted stapedotomy: micropick fenestration of the stapes footplate", Otolaryngology—Head and Neck Surgery, vol, 127-5, pp. 417-426, November 2002; D. Rothbaum, J. Roy, G. Hager, R. Taylor, and L. Whitcomb, "Task Performance in stapedotomy: Comparison between surgeons of different experience levels", Otolaryngology—Head and Neck Surgery, vol. 128-1, pp. 71-77, January 2003; I. lordachita, A. Kapoor, B. Mitchell, P. Kazanzides, G. Hager, J. Handa, and R. Taylor, "Steady-Hand Manipulator for Retinal Surgery", in MICCAI Workshop on Medical Robotics, Copenhagen, 2006, pp. 66-73 http://wwvv,isis.georgetown,edu/CAIMR/Workshops/miccai2006.htm; A. Uneri, M. Balicki, James Handa, Peter Gehlbach, R. Taylor, and I. lordachita, "New Steady-Hand Eye Robot with Microforce Sensing for Vitreoretinal Surgery Research", in BIOROB Conference, Tokyo, 2010, p. To appear) have been developed for use in microsurgical applications. In these systems, the surgeon and the robot both hold the surgical instrument. A force sensor detects forces exerted by the surgeon on the tool handle, and the robot moves to comply. Since the robot is actually doing the motion, motion is tremor-free and extremely precise. In the simplest use of such a robot, the surgeon would manipulate the tool just as in freehand surgery, using the tracking and information feedback methods described above. In other embodiments, the robot control may be modified to provide "virtual fixtures" limiting motion to prevent the implant tip from reaching the cochlear wall or to assist the surgeon in advancing the implant down the cochlea.

We also note that if the robot's base coordinate system remains fixed relative to the patient's skull, which is relatively easy to achieve if the patient's head is secured to a head-holding device, as is common in cochlear implant procedures, the robot may itself serve as a reference device. For example, the surgeon may position an imaging probe held by the robot into the cochlea using steady-hand guiding. An image would then be obtained and planning would be performed. The probe would then be replaced by an implant grasping tool, the implant would be grasped in a known location, and steady-hand guiding of the robot would then be used to insert the implant to the desired position.

Figure 6:
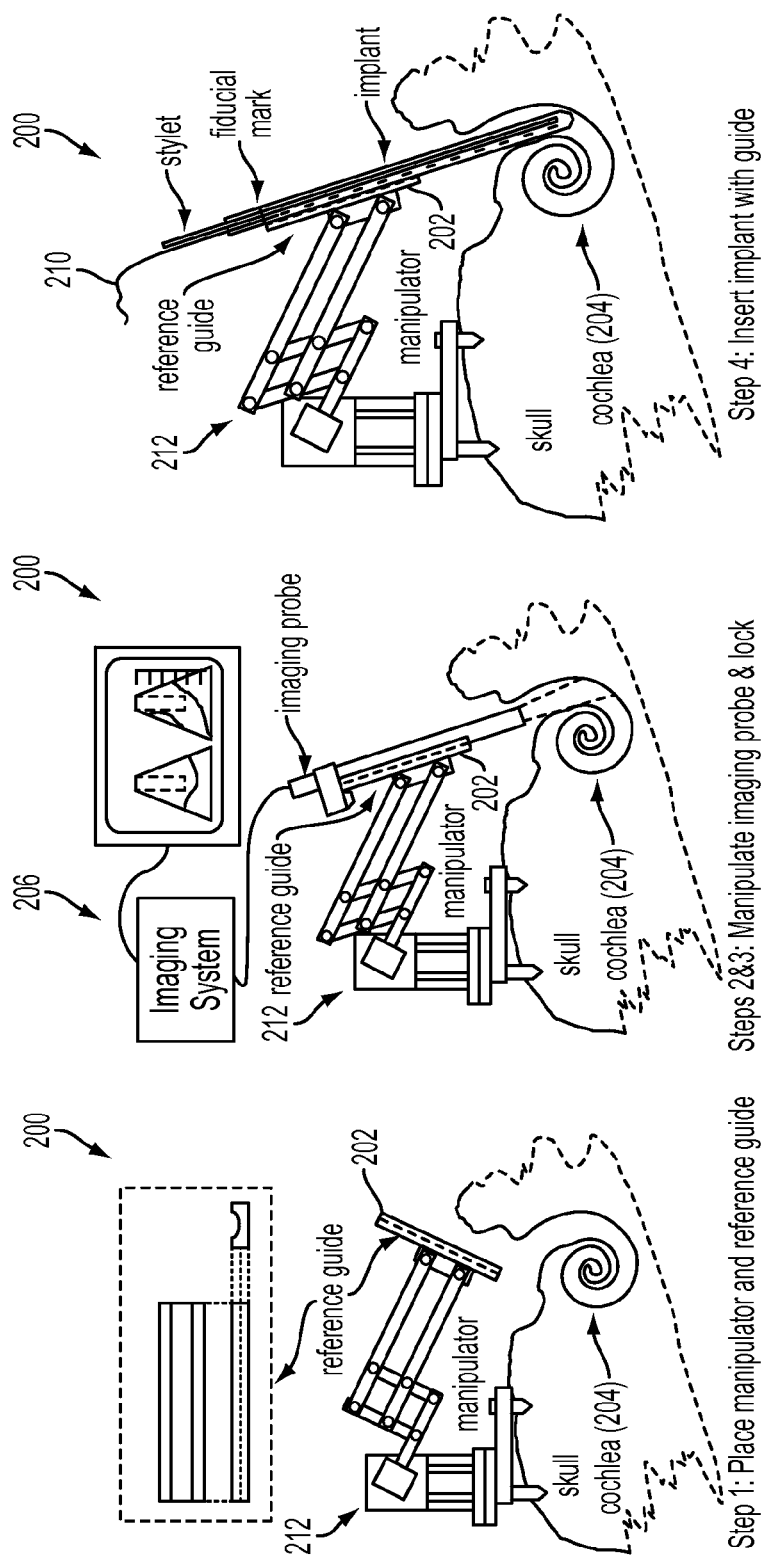
FIG. 6 is a schematic illustration of a system, method and associated devices for cochlear implant surgery according to another embodiment of the current invention.

Further Embodiments Combining Actively Manipulated Reference Guide Device for Imaging and Insertion FIG. 6 is a schematic illustration of a system for cochlear implant surgery 200 according to another embodiment of the current invention. The system for cochlear implant surgery 200 includes a reference guide device 202 having at least a portion adapted to be arranged at a fixed position relative to a cochlea 204 of a patient to provide a reference position. The system for cochlear implant surgery 200 also includes an image acquisition and processing system 206 adapted to acquire an image of at least a portion of the cochlea 204 relative to the reference device position and to provide an implant plan based at least partially on the acquired image. The system for cochlear implant surgery 200 further includes an implant system 208 adapted for implanting a cochlear lead array 210 using the reference device position and the implant plan. In this embodiment, a guide assembly 212 is attachable to the patient's skull. The guide assembly 212 can be a passive device that guides the surgeon and includes stops and/or locking mechanisms to lock it into particular configurations. In other embodiments it can be a partially automated assist device or a substantially fully automated robotic device. In this embodiment, the fiducial marker device 202 is a portion of the guide assembly 212. The guide assembly 212 can be configured to lock or otherwise hold the fiducial marker device 202 in a fixed or otherwise substantially known position such that the imaging and implanting can be correlated similar to the embodiments described above. The image acquisition and processing system 206 and implant system 208 can be similar to or the same as image acquisition and processing system 106 and implant system 108 in some embodiments.

In the embodiment illustrated in the FIG. 6, the imaging reference is mounted on a small adjustable and lockable manipulation aid, which is firmly mountable onto the patient's skull during the procedure and which is lockable into a suitable position relative to the cochlea so that the reference may serve as an insertion guide and position reference for the implant during insertion into the cochlea.

Actively Manipulated Reference Guide

Although, as will be seen from the description below, any manipulation device with sufficient degrees of freedom, mountability, and lockability may be used, the specific embodiment shown in the example of FIG. 6 is a miniature 5 degree-of-freedom remote-center-of-motion (RCM) manipulator comprising a 3 degree-of-freedom Cartesian stage for the translational (XYZ) motion, a revolute stage providing rotational motion by angle $\theta$ about $\vec{r}_0$, and a 5-bar kinematic linkage providing a second rotational motion by an angle $\phi$ about an axis $\vec{r}_\phi$. The manipulator is so constructed that the lines of the rotation axes $\vec{r}_\theta$, and $\vec{r}_\phi$ are perpendicular and intersect at the "RCM point" $\vec{p}_{RCM}$.

The reference guide in this embodiment is a simple mechanical guide affixed to the distal link of the RCM mechanism. A groove is cut into the surface of the reference guide so that when a cochlear implant is laid along the groove, the centerline axis of the implant—passes through the RCM point $\vec{p}_{RCM}$. The same groove and reference guide may be used to position an imaging probe so that images taken by the imaging probe have a known and fixed spatial relationship relative to the reference guide.

Any convenient means may be used to actuate (move) the degrees-of-freedom of the manipulator. One very simple means relies entirely on motive force provided by the surgeon. In this mode, each degree of freedom of the manipulator is a passive joint equipped with a locking mechanism. When the lock is disengaged, the surgeon can move the corresponding joint freely simply by grasping and moving the reference guide in the corresponding degree of freedom. When the lock is engaged, then the motion about the corresponding degree of freedom is prevented. In yet other embodiments, the mechanism may be designed so that one locking action will cause a plurality of the degrees of freedom to be locked simultaneously.

An alternative means of manual actuation of the manipulation device would use micrometer screws or their equivalents to move each degree of freedom of the mechanism. Such screws may be chosen so that the mechanism degrees of freedom are not "back drivable", i.e., so that they will not move unless the corresponding screws are turned. In this case, a separate locking mechanism is not required. Alternatively, the mechanism may be constructed so that the screws push against springs or their equivalent built into the mechanism. So long as the springs are sufficiently strong to overcome any forces exerted on the reference guide during imaging or during insertion of the implant, then a separate locking mechanism is again not required. One advantage of the use of micrometer screws to adjust the mechanism is that the adjustment can be more precise. Similarly, the chance of inadvertently moving the reference guide during locking can be eliminated. One advantage of completely passive manipulation of the probe is that it may possibly be faster for the surgeon. However, either method can be sufficiently efficient and accurate for particular applications.

The manipulation mechanism may be constructed using conventional pivot and sliding joints. Alternatively, it may be constructed using flexures for one or more of the degrees of freedom. Flexures an have many advantages for small, precise mechanisms. They have no run-out or backlash. It is often possible to manufacture them integrally with other structural elements of the mechanism, thus lowering manufacturing costs and simplifying assembly. It is possible to construct flexure-based mechanisms that inherently provide preload spring forces against which micrometer screw actuators can push. In designing flexure-based mechanisms it is important to design them so that the flexures will not experience fatigue fractures. This may be done by appropriate design methods that are well known to mechanical engineers. These include appropriate choices of materials, limiting joint excursions and radii of flexure curvature to ensure that flexure strains do not exceed elastic limits, and paying careful attention to the number of bending cycles to which a flexure will be subjected in use. We note that the size of the manipulation mechanism can potentially be made quite small and that it is possible to design the mechanism so that it can be affixed into a position and orientation relative to the patient's cochlea such that the total range of motion required to place the reference guide into the desired relationship to the cochlea can be small (e.g., ±5-10 mm of lateral motion and ±10-15 degrees of angular rotation).

The manipulation mechanism must typically be sterilized before clinical use. With suitable choice of materials, this may be accomplished by any of the usual methods for sterilizing surgical instruments. Alternatively, a low-cost mechanism may be produced as a single-use device and may be sterilized using gamma rays or other methods commonly employed for such devices.

One advantage of RCM mechanisms is that they permit translational and rotational alignments to be done without interfering with each other. For example, the translational degrees of freedom may be adjusted so that the RCM point $\vec{p}_{RCM}$ is positioned at the center of the opening into the cochlea and then locked. Then the rotational degrees of freedom may be adjusted so that the axis of an imaging probe placed into the reference guide (and, consequently, of the implant when placed into the reference groove in the reference guide) aligns with the desired insertion axis of the implant into the cochlea. The rotational degrees of freedom may then be locked and further small adjustments to the translational position may be made. The process may be repeated until the desired insertion path is obtained.

However, we note that RCM manipulation mechanisms are not necessary to practice the basic method in these embodiments of this invention. Any mechanism providing sufficient degrees of freedom to align the reference guide to the cochlea and then capable of holding the guide stably in this relative position and orientation during insertion may be used. One example would be a simple lockable bead chain arrangement or variations well known in the mechanical engineering art. Another would be a serial-link lockable device similar to the many lockable instrument-holding devices known in the surgical art (e.g., the "IronIntern®" manufactured and marketed by Automated Medical Products Corp., P.O. Box 2508, Edison, N.J. 08818, http://www.ironintern.com/amp/) though on a smaller physical scale. Yet another example would be a parallel-link mechanism with lockable links, again using any one of many kinematic design principles well known in the art.

We also note that motors, piezoelectric actuators, hydraulic cylinders, or other means well known in to mechanical engineers may actively actuate the manipulation mechanism. The surgeon can control the motion of the resulting robotic mechanism by means of handover-hand "steady hand" cooperative control or by teleoperator control, using any convenient teleoperation "master" to command motions. See, for example:

- R. H. Taylor, P, Jensen, L. L. Whitcomb, A. Barnes, R. Kumar, D. Stoianovici, P, Gupta, Z. X. Wang, E. deJuan, and L. R. Kavoussi, "A Steady-Hand Robotic System for Microsurgical Augmentation", *International Journal of Robotics Research*, vol. 18-12, 1999
- P. J. Berkelman, D. L. Rothbaum, J. Roy, Sam Lang, L, L. Whitcomb, G. Hager, P. S. Jensen, R. H. Taylor, and J. Niparko, "Performance Evaluation of a Cooperative Manipulation Microsurgical Assistant Robot Applied to Stapedotomy", in *Medical Image Computing and Computer-Assisted Interventions (MICCAI* 2001), Utrecht, 2001, pp. 14264429
- D. L. Rothbaum, J. Roy, P. Berkelman, G. Hager, D. Stoianovici, R. H. Taylor, L. L. Whitcomb, M. Howard Francis, and J. K. Niparko, "Robot-assisted stapedotomy: micropick fenestration of the stapes footplate", *Otolaryngology—Head and Neck Surgery*, vol, 127-5, pp. 417-426, November 2002.
- D. Rothbaum, J. Roy, G. Hager, R. Taylor, and L. Whitcomb, "Task Performance in stapedotomy: Comparison between surgeons of different experience levels", *Otolaryngology—Head and Neck Surgery*, vol. 128-1, pp. 71-77, January 2003
- I. lordachita, A. Kapoor, B. Mitchell, P. Kazanzides, G. Hager, J. Handa, and R. Taylor, "Steady-Hand Manipulator for Retinal Surgery", in *MICCAI Workshop on Medical Robotics*, Copenhagen, 2006, pp. 66-73 http://wwvv,isis.georgetown,edu/CAIMR/Workshops/miccai2006.htm
- Uneri, M. Balicki, James Handa, Peter Gehlbach, R. Taylor, and I. lordachita, "New Steady-Hand Eye Robot with Microforce Sensing for Vitreoretinal Surgery Research", in *BIOROB Conference*, Tokyo, 2010, p. To appear Methods according to some embodiments of the current invention use the above-described hardware to assist the surgeon in introducing the implant into the cochlea. In outline, a method according to an embodiment of the current invention includes:

1. Place the base of the combined manipulator and reference guide mechanism so that the point is positioned approximately at the entrance to the cochlea and the axis of the reference groove approximately aligns with the desired insertion axis of the implant into the cochlea, and then fix the base of the manipulator so that it maintains this fixed spatial relationship with the cochlea during the procedure.
2. Place an imaging probe into a known spatial relationship with the reference guide and acquire one or more images of the cochlea.
3. Use information from the images to position the manipulation mechanism so that the position and direction of the reference guide aligns with the cochlea in a desired spatial relationship to assist insertion into the cochlea.
4. While maintaining the reference guide in the desired spatial relationship relative to the cochlea, use the reference guide to assist the surgeon in inserting the implant into the cochlea.

In practice, Steps 2 and 3 are performed concurrently or in multiple iterations until the desired spatial relationship is achieved. Depending on the design of the manipulation mechanism, the mechanism may need to be locked at this point. Alternatively, the mechanism may naturally stay in this posture unless explicitly moved by the surgeon. Similarly, Steps 2 and 3 may be combined in part with Step 1. A more detailed description of these steps is as follows.

Step 1: Place Manipulator and Reference Guide

In this step, the surgeon places the base of the combined manipulator and reference guide mechanism so that the point $\vec{p}_{RCM}$ is positioned approximately at the entrance to the cochlea and the axis of the reference groove approximately aligns with the desired insertion axis of the implant into the cochlea, and then fixes the base of the manipulator so that it maintains this fixed spatial relationship with the cochlea during the procedure.

The manipulator and reference guide should be placed so that the imaging probe used in Steps 2 and 3 does not come into contact with the cochlea during the repositioning in Step 3. This is easily accomplished with an RCM manipulation mechanism but may also be accomplished with a non-RCM mechanism, especially if suitable care is taken by the surgeon during manipulation.

One convenient method for doing the placement relies on the surgeon's natural visual assessment of the surgical field and his or her natural hand-eye coordination, using the reference guide as a visual indicator. For example, the degrees-of-freedom of the manipulator can be set to the approximate center of their motion range and then locked (if necessary to hold them in this position). Optionally, the imaging probe or another indicating device can be placed into the reference guide groove, with the end of the probe placed at the RCM point $\vec{p}_{RCM}$ (in the case that an RCM manipulator design is used) or at another convenient point. The surgeon can then manually place the manipulator base so that the probe is in the desired spatial relationship to the cochlea and secure the base to the patient's skull or otherwise secure it so that the base remains in a fixed spatial relationship relative to the cochlea.

If the imaging probe is in place during this step, then live images of the cochlea may be acquired and displayed to assist the surgeon in achieving approximately the desired alignment. One possible optional imaging device might comprise a laser or LED beam generating device shining a bright visible beam of light co-axial with the eventual insertion axis of the implant when it is placed into the reference guide groove. Alternatively, in some designs, such a light beam generating capability may be integrated into the imaging probe itself. This option may be especially easy to achieve if the imaging probe is itself an optical imaging probe, such as an OCT probe.

The sketch in FIG. 6 implies the use of small screws or spikes to secure the manipulation mechanism and reference guide to the patient's skull. However, the specific choice of means to achieve this function is not an essential element of this invention. Any means of securing the manipulation device's base into a fixed spatial relationship to the patient's cochlea during imaging and insertion may be used. Examples may include: alternative means for attaching the mechanism directly to the patient's head; mounting the mechanism onto a head-holding device used to secure the patient's head during surgery (e.g., the Mayfield® skull clamp, http://www.integrals.com/home/catalogs.aspx); or mounting to the operating table if the patient's skull is held fixedly to the table. Generally, a short chain of connections between the cochlea and manipulator base is to be preferred, since this provides less opportunity for error accumulation from small motions in each connection. If desired, an auxiliary means of support may be provided to bear some of the weight of the manipulation device, so that a connection to the skull is simply needed to provide a stable spatial relationship. However, in many embodiments of the current invention, the actual weight and size of the manipulation device will be small enough so that auxiliary supports are not needed.

Step 2: Imaging of the Cochlea

In this step, the surgeon will place the imaging probe into a known spatial relationship with the reference guide and use it to acquire one or more images of the cochlea.

Many methods may be used to place the imaging probe into a known spatial relationship with the reference guide. One very simple embodiment is illustrated schematically in FIG. 6. In this embodiment, the imaging probe comprises a cylindrical shaft with the same diameter as the implant, so that the central axis of the probe aligns with the central axis of the implant when it is placed into the groove. A reference tab on the proximal end of the imaging probe engages with reference surfaces at the proximal end of the reference guide so that the displacement of the probe along the groove is determined and the rotation of the probe about its axis is constrained to one or more preferred and known orientations. Alternatively, index marks or sensors may be used to measure the position and orientation of the probe relative to the reference guide, and this information may then be used to determine a transformation between image coordinates and a coordinate system associated with the reference guide. In still other embodiments, the proximal end of the reference guide may comprise an adjustable mechanical guide to assist in probe alignment. For simplicity in description of embodiments of this invention, we will assume that images are produced with image coordinates in known spatial relationship to the reference guide, either from design of the probe or by measurement and mathematical correction in a computer.

Any imaging modality capable of producing images of the cochlea may be used. In one embodiment, the images would be OCT images produced using a fiber-optic imaging bundle probe similar to that described by Han et al. (J.-H. Han, X. Liu, C. G. Song, and J. U. Kang, "vol. 45, no, 22, pp., October, 2009 "Common path optical coherence tomography with fibre bundle probe", *Electronics Letters*, vol. 45-22, pp. 1110-1112, October 2009 NIHMSID 188391). The fibers comprising this probe may be interrogated to produce "A-mode" (i.e., single OCT distance scans), "B-mode" (i.e., cross-sectional images), or "C-mode" 3D volumetric) images. In yet another embodiment, the imaging probe may be a high frequency imaging ultrasound probe. Ultrasound imaging probes may be designed to produce A-mode, B-mode", or C-mode images. We note that one way to produce a B-mode or C-mode image is to scan an A-mode imaging device to produce multiple A-mode lines that are then combined to make a B-mode or C-mode image, using methods well known in the imaging art. Similarly, a C-mode image may be produced by scanning a B-mode imaging device. Such scanning may be accomplished by a special-purpose actuator integrated into the probe. Similarly, we note that B-mode or A-mode images may be obtained trivially from C-mode images by sub-sampling techniques well known in the art.

Two advantages of both OCT and ultrasound imaging modalities are that they permit real time imaging and visualization of the anatomy and that they do not impart potentially harmful radiation to the patient or to the surgeon. For this reason, they are preferred to X-ray imaging. However, X-ray tomographic images may also be obtained, as discussed earlier. In this case, the reference guide should comprise sufficient fiducial geometry so that the transformation between image and reference guide coordinates may be determined.

Step 3: Alignment of the Reference Guide

The surgeon will use information from the images of the cochlea to position the manipulation mechanism so that the position and direction of the reference guide aligns with the cochlea in a desired spatial relationship to assist insertion into the cochlea.

As mentioned above, real-time imaging modalities such as OCT or ultrasound are preferred. We will first describe the method for the use of such modalities and then describe modifications for the case where X-ray tomography or other non-real time volumetric imaging modalities (e.g., MRI) might be used.

In an embodiment, the images produced by the imaging probe are displayed to the surgeon on a computer monitor, combined with computer graphics indicating the position of the implant when it is in a known spatial relationship to the reference guide. Typically, this spatial relationship will correspond to the position of the implant where fiducial marks on the implant align with reference points, marks, or surfaces on the reference guide. In the sketch shown in FIG. 6, two cross-sectional B-mode images of the cochlea are displayed, and computer graphics show corresponding cross-sectional images of the implant, indicating where it would be relative to the anatomic structures shown in the images if it were placed into the specified spatial relationship relative to the reference guide. Such pairs of B-mode images may be obtained from a C-mode image by sub-sampling or from a specially constructed probe. Alternatively, they may be obtained sequentially. We note that other image displays and computer graphics overlays may be constructed, based on the characteristics of the imaging modality. For example 3D models of the implant may be displayed with volumetric renderings of C-mode images. Or very simple computer graphics elements (such as lines and cross-hairs) may be substituted for graphic renderings of the implant. However, cross-sectional displays of implant shape combined with cross-sectional images have been shown to be effective in other image-based planning applications (e.g., R. H. Taylor, H. A. Paul, P. Kazandzides, B. D. Mittelstadt, W. Hanson, J, F. Zuhars, B. Williamson, B. L. Musits, E. Glassman, and W. L, Bargar, "An Image-directed Robotic System for Precise Orthopaedic Surgery", *IEEE Transactions on Robotics and Automation*, vol. 10-3, pp, 261-275, 1994). Although two orthogonal B-mode slices should be sufficient for the current purpose, we note that it is a straightforward matter to generate multiple cross-sectional slices and associated graphics from a C-mode volume if this is desired for the surgeon.

Using the display shown in FIG. 6, the surgeon would manipulate the manipulation mechanism (and, hence, the spatial relationship between the reference guide and the cochlea) while also obtaining a plurality of images, until the computer graphics overlay on the images indicates that the reference guide is in the proper spatial relationship with the cochlea. Once the desired endpoint and central axis of the implant relative to the cochlea are determined, additional images or cross-sections may be obtained or displayed to determine the desired rotational orientation of deployment for the implant relative to the reference guide as it curls into the cochlea.

If only B-mode images are obtainable with the imaging probe, multiple B-mode slices may be obtained readily by rotating the imaging probe about its axis, and either measuring this rotation or providing multiple referencing surfaces or geometry on the probe carrier and reference guide.

In one convenient embodiment, a B-mode probe may be combined conveniently with an RCM manipulation mechanism. In this case, the B-mode probe would first be placed in an orientation aligned with one rotational degree of freedom of the RCM mechanism, and the other degree of freedom would be locked (or not moved). The surgeon would then align the probe in this direction, based on real-time B-mode images and computer graphics. The probe would then be placed to align with the other degree of freedom, which would be manipulated while the first remains fixed. This process would be iterated until a desired position and axis alignment is obtained. Additional B-mode images may then be obtained by rotating the probe about its axis to determine the desired plane of deployment of the implant.

An A-mode probe may potentially be used as well, although in this case additional information (e.g., from sensing of manipulator motion or use of calibrated micrometer dials) may be used to supplement the information used to obtain a desired alignment.

Figure 1B:
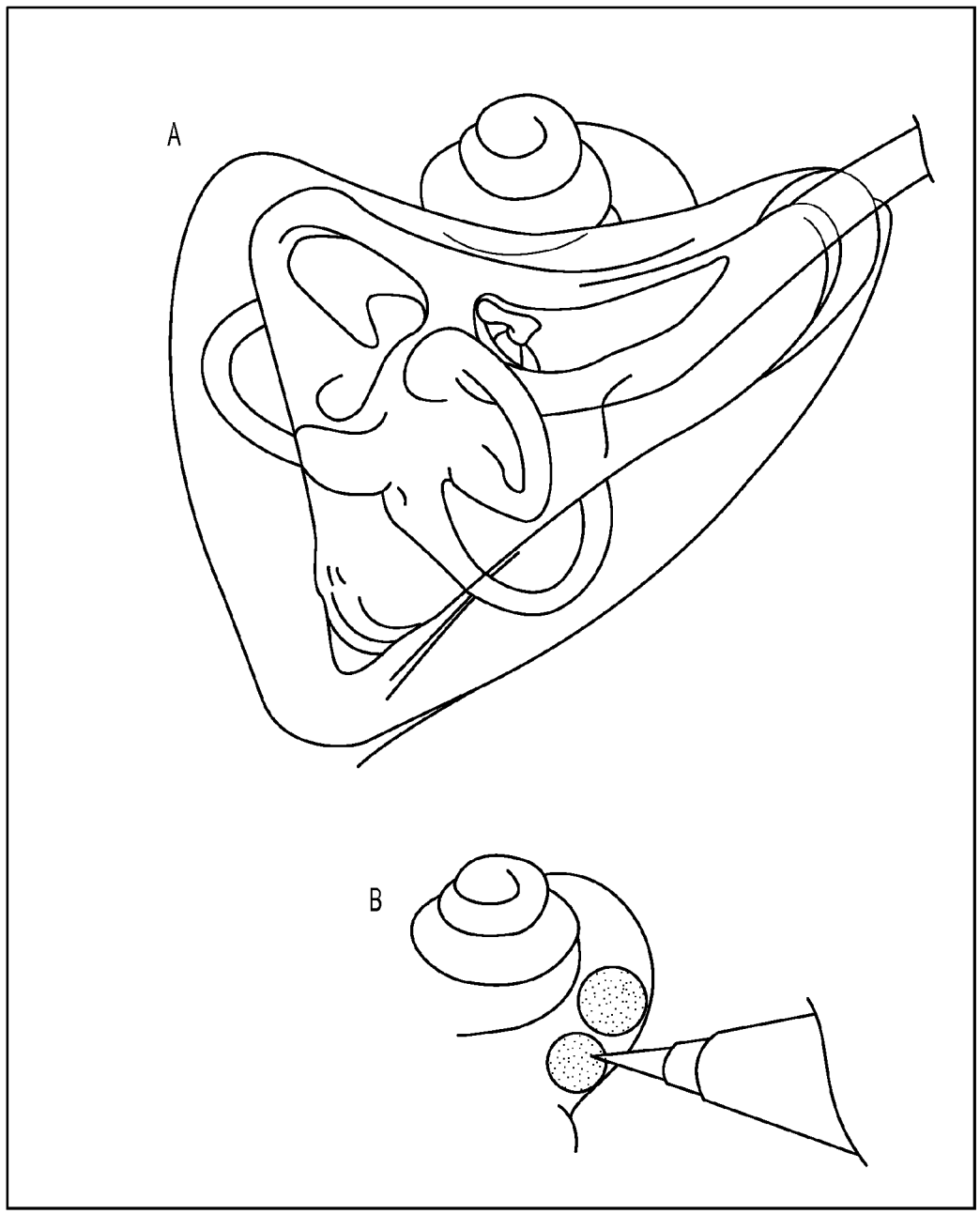
Figure 1C:
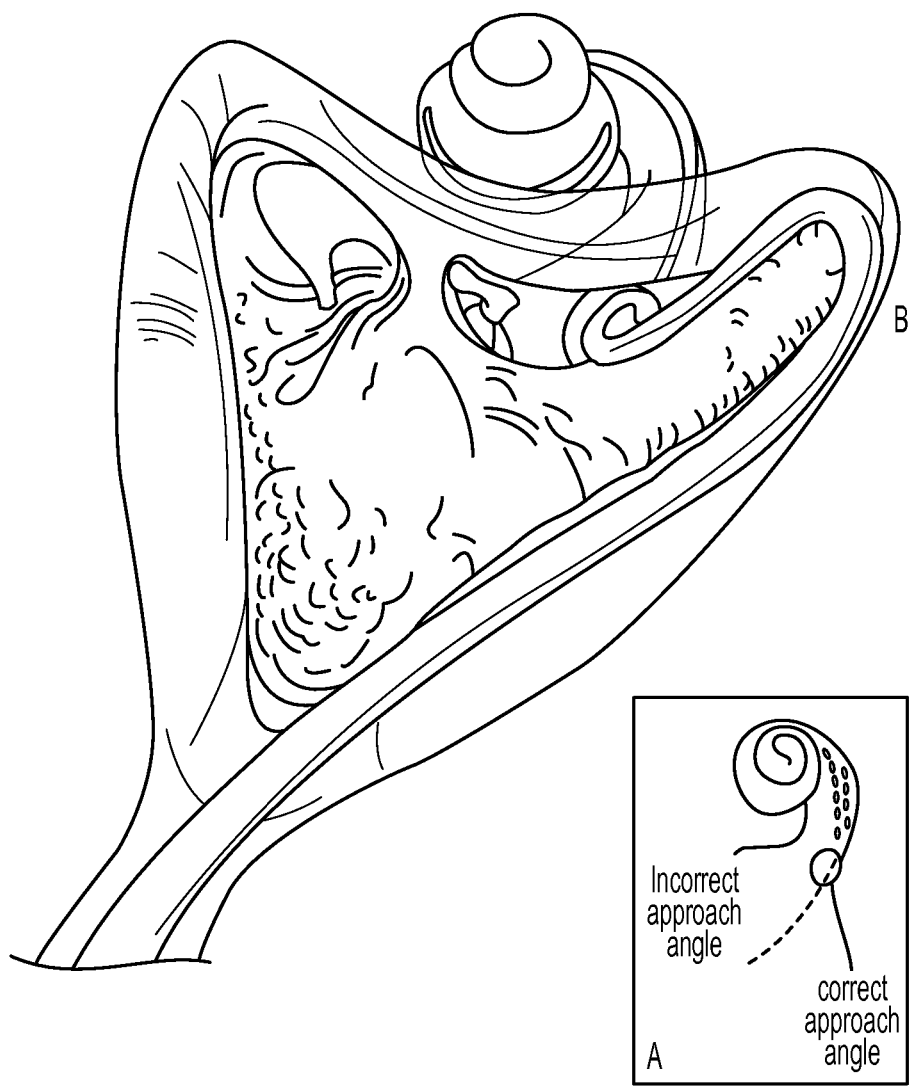
Figure 2:
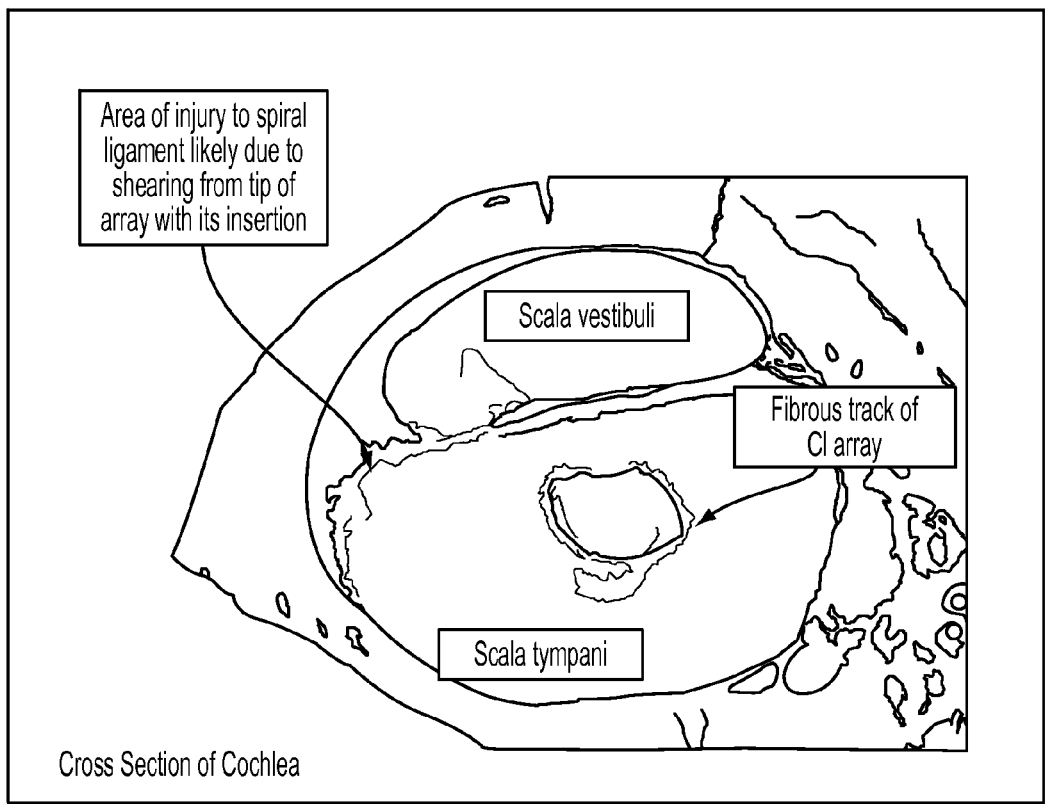
FIG. 2 shows a cross sectional view of structures that have to be navigated during a cochlear implant procedure.

In the case where a single volumetric image is obtained (e.g., from X-ray cone beam tomography). The surgeon would use a mouse, joystick, or other input device to manipulate a graphic rendering of the implant (or other graphical information) on a display screen showing views of the image in order to determine the desired position of the implant upon insertion into the cochlea. From the position and orientation of the reference guide relative to volumetric image coordinates, the computer would compute a motion of the reference guide (and, hence, of the manipulation mechanism) that would bring the reference guide into the desired alignment with the cochlea. The surgeon would then move the manipulation mechanism to achieve this desired motion. This could be accomplished using simple graduated micrometer adjustments on the manipulator, feedback sensing on the manipulator degrees of freedom, or any of the sensing and feedback means discussed under embodiments discussed earlier (e.g., those for FIG. 1).

Step 4: Insertion of the Implant

Once the reference guide is in the desired spatial relationship relative to the cochlea, the surgeon will use the reference guide to assist him or her in inserting the implant into the cochlea, while the reference guide remains fixed relative to the cochlea. We note that it is not necessary for the reference guide to tightly constrain the implant, since the surgeon will still be doing the actual manipulation. Instead, it is intended to provide a guide or reference to assist the surgeon in achieving the correct insertion path so that the end of the implant is at the correct position in the cochlea when the surgeon begins to deploy it around the curl of the cochlea. However, it is likely that the surgeon will slide the implant along the groove until the correct insertion depth is obtained.

As noted above, the reference guide may be maintained in its desired spatial relationship relative to the cochlea either by locking the manipulation mechanism or, depending on the particular means used to manipulate it (e.g., screw actuators), simply by not moving it.

The simplest means for using the reference guide is for the surgeon to rely upon reference marks on the implant itself. For example, the implant would be inserted into the cochlea until a reference mark on the implant aligns with a corresponding mark on the reference guide. Additional marks on the reference guide may be used to assist the surgeon in achieving the desired orientation about the implant axis prior to deployment.

Alternatively, a simple tool may be devised to grasp the implant or insertion stylet or sheath in a known spatial relationship. This tool could then be mated to the reference guide using simple mechanical methods well know in the mechanical engineering art. This alignment may be achieved using the same methods used to align the probe. Perhaps the simplest would be a series of index marks on the proximal end of the guide showing different orientation rotations. The tool would comprise a tab or index mark that would be aligned to one of these index marks.

Further Embodiments and Combinations

The methods and apparatus disclosed in this invention may be used in multiple combinations in order to achieve the goals of the invention. For example, preoperative or intraoperative cone-beam tomographic images of the skull and cochlea may be obtained and used to determine a desired implant placement and insertion path. Intraoperative OCT or ultrasound images may be obtained subsequently using the imaging probe/manipulator reference combination described above. These images may be co-registered to the tomographic images to provide a fused computer representation of the patient's cochlea whose coordinates are known relative to the reference guide device. Any of the methods described above may then be used to guide the implantation relative to the guide. For example, the mechanism may be moved by a desired amount to align the reference guide groove with the desired insertion path, The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A system for cochlear implant surgery, comprising:
   a reference device having at least a portion adapted to be arranged at a fixed position relative to a cochlea of a patient to provide a reference position;
   an image acquisition and processing system adapted to acquire an intraoperative image of at least a portion of said cochlea relative to said reference position and to provide an implant plan based at least partially on the acquired intraoperative image; and
   an implant system adapted for implanting a cochlear lead array using said reference position and said implant plan,
   wherein said image acquisition and processing system comprises an optical coherence tomography imaging probe.

2. A system for cochlear implant surgery according to claim 1, further comprising a subsystem for measuring the position of at least one of an implant or implant insertion device relative to said reference position.

3. A system for cochlear implant surgery according to claim 2, further comprising a computer and display for informing a surgeon of the position of the implant or insertion device relative to the reference position.

4. A system for cochlear implant surgery according to claim 2, further comprising an auditory signaling device for informing a surgeon of the position of the implant or insertion device relative to the reference position.

5. A system for cochlear implant surgery according to claim 1, wherein said reference device is structured to be fixable to and removable from said patient during surgery.

6. A system for cochlear implant surgery according to claim 1, wherein said reference device is a spring-clip reference device that is insertable into an opening made during at least one of a cochleostomy or mastoidectomy surgical procedure and reconfigurable to remain fixed during a cochlear implant procedure.

7. A system for cochlear implant surgery according to claim 6, wherein said spring-clip reference device is insertable into a cochlear opening.

8. A system for cochlear implant surgery according to claim 1, wherein said reference device is at least a portion of a guide assembly that is attachable to said patient's skull.

9. A system for cochlear implant surgery according to claim 1, wherein said guide assembly is a lockable guide assembly configured to be locked to hold said reference device in a fixed position relative to said cochlea.

10. A system for cochlear implant surgery according to claim 1, wherein said guide assembly is a motion-assist guide assembly.

11. A system for cochlear implant surgery according to claim 1, wherein said guide assembly is a robotic guide assembly.

12. A system for cochlear implant surgery according to claim 1, wherein said image acquisition and processing system is configured to provide a three-dimensional image of at least part of an insertion area of said cochlea.

13. A system for cochlear implant surgery according to claim 12, wherein said image acquisition and processing system is configured to provide at least one distance measurement from the optical coherence tomography imaging probe to a portion of the cochlea.

14. A system for cochlear implant surgery according to claim 12, wherein said image acquisition and processing system is configured to provide a plurality of distance measurements from the optical coherence tomography imaging probe to portions of the cochlea.

15. A system for cochlear implant surgery according to claim 1, wherein said image acquisition and processing system comprises an external imaging system.

16. A system for cochlear implant surgery according to claim 15, wherein said external imaging system is at least one of a cone-beam x-ray system, a computed tomography x-ray system or an magnetic resonance imaging system.

17. A system for cochlear implant surgery according to claim 1, wherein said implant system comprises an insertion device having calibration marks to indicate a depth of insertion of the tip of the insertion device relative to said reference position of said reference device.

18. A system for cochlear implant surgery according to claim 17, wherein said insertion device comprises a stylet.

19. A system for cochlear implant surgery according to claim 17, wherein said insertion device comprises a sheath.

20. A system for cochlear implant surgery according to claim 1, wherein said reference device comprises a guide for receiving alternately an imaging probe and an insertion device for sequentially inserting said optical coherence tomography imaging probe and said insertion device.

21. A system for cochlear implant surgery according to claim 20, wherein said insertion device comprises a stylet.

22. A system for cochlear implant surgery according to claim 20, wherein said insertion device comprises a sheath.

23. A system for cochlear implant surgery according to claim 20, wherein said reference device is at least a portion of a guide assembly that is attachable to said patient's skull.

24. A system for cochlear implant surgery according to claim 20, wherein said guide assembly is a lockable guide assembly configured to be locked to hold said reference device in a fixed position relative to said cochlea.

25. A system for cochlear implant surgery according to claim 20, wherein said guide assembly is a motion-assist guide assembly.

26. A system for cochlear implant surgery according to claim 20, wherein said guide assembly is a robotic guide assembly.

27. A system for cochlear implant surgery according to claim 20, wherein said optical coherence tomography imaging probe comprises an optical coherence tomography sensor.

* * * * *